US00PP23686P2

(12) United States Plant Patent
Bradford

(10) Patent No.: US PP23,686 P2
(45) Date of Patent: Jun. 25, 2013

(54) INTERSPECIFIC TREE NAMED 'PLUMSWEET XIV'

(50) Latin Name: ***Prunus* sp.**
Varietal Denomination: Plumsweet XIV

(76) Inventor: Lowell Glen Bradford, Le Grand, CA (US)

( * ) Notice: Subject to any disclaimer, the term of this patent is extended or adjusted under 35 U.S.C. 154(b) by 62 days.

(21) Appl. No.: 13/374,017

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP19,796 P2 3/2009 Bradford

*Primary Examiner* — Annette Para

(57) ABSTRACT

The present invention relates to an interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the mid season. The present variety's abundance of blossoms and moderate pollen production entices strong bee activity to facilitate pollination. The fruit matures under the ecological conditions described during late July, with first picking on Jul. 25, 2011, and will hang on the tree for at least fifteen more days. The fruit is uniformly medium in size, red over a green background in skin color, clingstone in type, globose in shape, full red in flesh color, very firm and crisp in texture, and excellent in flavor.

1 Drawing Sheet

Botanical classification: *Prunus* sp.
Varietal denomination: 'PLUMSWEET XIV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet XIV'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2003 one tree of '26P166' (unpatented) plum was crossed by me in this manner. To pollinate this isolated tree, I selected bouquets from several sources of apricot and interspecific hybrid trees without keeping specific written details. Upon reaching maturity the fruit from this plum tree was harvested and the seeds were removed, cracked, stratified and germinated as a group with the label "H13". They were grown as seedlings on their own root in my greenhouse and upon reaching dormancy transplanted to a cultivated area of my experimental orchard located near Le Grand, Calif. in Merced County (San Joaquin Valley). During the summer of 2007 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '26P166' plum (unpatented) by being self-unfruitful and producing fruit that is firm, juicy, mostly red in skin color, and ripens in the mid season, but is quite distinguished therefrom by producing fruit that is sweeter, firmer, and dark red instead of yellow in flesh color.

The present variety is most similar to 'Plumsweet XI' (U.S. Plant Pat. No. 19,796) interspecific tree by being self-unfruitful and producing fruit that is sweet and excellent in flavor, red in primary skin color, and clingstone in type, but is quite distinguished therefrom by blooming about 7 days later and by producing fruit that is globose instead of oblate in shape, that has more green in the background skin color, and that matures about twenty-two days later.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the mid season. The present variety's abundance of blossoms and moderate pollen production entices strong bee activity to facilitate pollination. The fruit matures under the ecological conditions described during late July, with first picking on Jul. 25, 2011, and will hang on the tree for at least fifteen more days. The fruit is uniformly medium in size, red over a green background in skin color, clingstone in type, globose in shape, full red in flesh color, very firm and crisp in texture, and excellent in flavor.

DRAWING

The accompanying photograph consists of four whole fruits positioned to display the characteristics of the skin color and form, two half fruits divided to reveal the flesh and stone, typical leaves, and two insets depicting the buds and flower blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 30, 2011, on the original tree during its eighth growing season. The flower and bud descriptions were developed during the previous blooming season. All major color code designations are by reference to the Inter-Society Color Council, National Bureau of Standards. Common color names are also used occasionally.

PARENTAGE

Seed parent: '26P166' plum (unpatented).
Pollen parent: Unknown.

TREE

Size: Medium, reaching and maintaining a height of 12' [3.66 m.] and a spread of 5' [1.52 m.] after eight growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming plum or interspecific, such as 'Blackred V' interspecific tree (U.S. Plant Pat. No. 19,576).

Bearing: Regular bearer, with no crop failures observed.

Trunk:

- *Size*.—Large, reaching a maximum diameter of 4½" [114.3 mm.] after the eight growing season.
- *Texture*.—Medium.
- *Bark color*.—A Dark grayish brown [62. d.gy.Br] and Dark brown [59. d.Br] variegation with Light yellowish brown [76. l.yBr] crevices present.
- *Lenticels*.—Approximate Number Per Square Inch: 10. Color: Light yellowish brown [76. l.yBr]. Average Size: ⅛" [3.2 mm.] to 7/16" [11.1 mm.]. Shape: Eye-shaped, elongated.

Branches:

- *Size*.—Diameter of limb is 2¼" [57.2 mm.] measured 12" above the crotch, 1¼" [31.8 mm.] measured 12" above the first fork.
- *Texture*.—Smooth on first and second year wood, increasing roughness with age.
- *Color*.—1st Year Wood Topside: Grayish red [19. gy.R]. 1st Year Wood Underside: Brilliant yellow green [116. brill.YG]. 2$^{nd}$ Year Wood: A Strong yellowish brown [74. s.yBr] and Strong yellow green [117. s.YG] variegation.
- *Lenticels*.—Number Per Square Inch: About 60 on second year wood. Color: Light yellowish brown [76. l.yBr]. Size: 1/64" [0.4 mm.] to 1/16" [1.6 mm.]. Shape: Rectangular, elongated.

Leaves:

- *Size*.—Medium. Average Length: 4" [101.6 mm.]. Average Width: 1⅝" [41.3 mm.].
- *Arrangement*.—Alternate.
- *Thickness*.—Medium.
- *Form*.—Elliptical.
- *Apex*.—Acuminate.
- *Base*.—Some rounded, some acute.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: 9/16" [14.3 mm.]. Average Thickness: 1/16" [1.6 mm.]. Color: Light yellow green [119. l.YG].
- *Stipules*.—Number: Typically 2 per leaf. Average Length: 5/16" [7.9 mm.]. Color: Brilliant yellow green [116. brill.YG].
- *Glands*.—Number: Mostly 2 per leaf. Position: Alternately positioned at the intersection of the petiole and the leaf blade. Size: Small. Form: Globose. Color: Brilliant yellow green [116. brill.YG] becoming Grayish brown [61. gy.Br] in the center with age.
- *Leaf buds*.—Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.

- *Average flower diameter*.—1" [25.4 mm.].
- *Number of petals*.—Five, no double blossoms observed.
- *Petal shape*.—Oval to circular.
- *Petal margin*.—Entire, somewhat wavy.
- *Average petal diameter*.—7/16" [11.1 mm.].
- *Average petal length*.—½" [12.7 mm.].
- *Petal apex*.—Rounded.
- *Petal base*.—Obtuse.
- *Petal color*.—White [263. White] on both sides.
- *Anther color*.—Light yellow [86. l.Y].
- *Stigma color*.—Light greenish yellow [101. l.gY].
- *Sepal color*.—Light yellow green [119. l.YG].
- *Sepal length*.—3/16" [4.8 mm.].
- *Sepal width*.—5/32" [4.0 mm.].
- *Sepal apex*.—Rounded to elliptical to match the width and length.
- *Sepal margin*.—Fairly smooth to the naked eye, slightly serrate when magnified.
- *Average pistil length*.—½" [12.7 mm.], some blanks observed.

*Average stamen length.*—9/16" [14.3 mm.].
*Fragrance.*—Moderate.
*Pollen production.*—Moderate.
*Blooming period.*—Medium, two days after 'Black Amber' plum (unpatented).
*Onset of bloom.*—One percent on Feb. 27, 2011.
*Date of full bloom.*—Mar. 8, 2011.
*Duration of bloom.*—One to two weeks, dependent on ambient temperature.
*Bloom density.*—Heavy.
*Number per cluster.*—2 to 8, average 4.

FRUIT

Maturity when described: Firm ripe, Jul. 30, 2011.
Date of first picking: Jul. 25, 2011.
Date of last picking: Aug. 10, 2011.
Size: Uniform, Medium.
*Average diameter axially.*—2 3/16" [55.6 mm.].
*Average diameter across cheek plane.*—2 7/16" [61.9 mm.].
*Average diameter across suture plane.*—2 3/8" [60.3 mm.].
*Typical weight.*—4.6 ounces [130.4 grams].
Form: Uniform, globose, symmetrical.
*Longitudinal section form.*—Slightly elliptical to round.
*Transverse section through diameter.*—Round.
Suture: A distinct line located in a shallow trough extending from the base to the apex.
Ventral surface: Rounded, very slightly lipped toward the base.
Lips: Equal.
Cavity: Flaring, rounded, suture showing on one side.
*Depth.*—5/16" [7.9 mm.].
*Breadth.*—15/16" [23.8 mm.].
Base: Truncate.
Apex: Rounded.
Pistil point: An inconspicuous Light yellowish brown [76. l.yBr] dot.
Stem: Medium.
*Average length.*—5/16" [7.9 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—Slight in wet season.
*Color.*—Dark red [16. d.R] over a Dark greenish yellow [103. d.gY] background with heavy Grayish greenish yellow [105. gy.gY] freckling throughout.
*Bloom.*—Abundant.
Flesh:
*Color.*—Dark red [16. d.R] throughout.
*Surface of pit cavity.*—Covered with Very deep red [14. v.deep R] broken fibers when twisted from stone.
*Amygdalin.*—Moderate.
*Juice.*—Abundant, rich.
*Texture.*—Firm, crisp.
*Fibers.*—Few, tender.
*Ripens.*—Fairly even.
*Flavor.*—A tasty blend of acid and sugar, typically 19 brix.
*Aroma.*—Slight.
*Eating quality.*—Excellent.

STONE

Type: Clingstone.
Form: Oval.
Hilum: Narrow, oval.
Base: Obtuse.
Apex: Acute, with a sharp 1/8" [3.2 mm.] tip.
Sides: Equal.
Surface: Rough throughout with a few ridges near the base.
External color of stone: Moderate orange yellow [71. m.OY].
Pit wall color when cracked: Light yellowish brown [76. l.yBr].
Cavity surface color: Brownish orange [54. brO].
Average pit wall thickness: 1/16" [1.6 mm.].
Average width: 3/4" [19.1 mm.].
Average length: 1 1/8" [28.6 mm.].
Average breadth: 5/16" [7.9 mm.].
Tendency to split: None observed.
Kernel:
*Form.*—Oval.
*Skin color.*—Light yellow [86. l.Y] when dry.
*Pellicle color.*—Dark grayish yellow [91. d.gy.Y].
*Vein color.*—Light orange yellow [70. l.OY].
*Taste.*—Somewhat bitter.
*Viable.*—Yes.
*Average width.*—1/2" [12.7 mm.].
*Average length.*—5/8" [15.9 mm.].
*Amygdalin.*—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Plumsweet XI' (U.S. Plant Pat. No. 19,796) interspecific tree by being self-unfruitful and producing fruit that is sweet and excellent in flavor, red in primary skin color, and clingstone in type, but is quite distinguished therefrom by blooming about 7 days later and by producing fruit that is globose instead of oblate in shape, that has more green in the background skin color, and that matures about twenty-two days later.

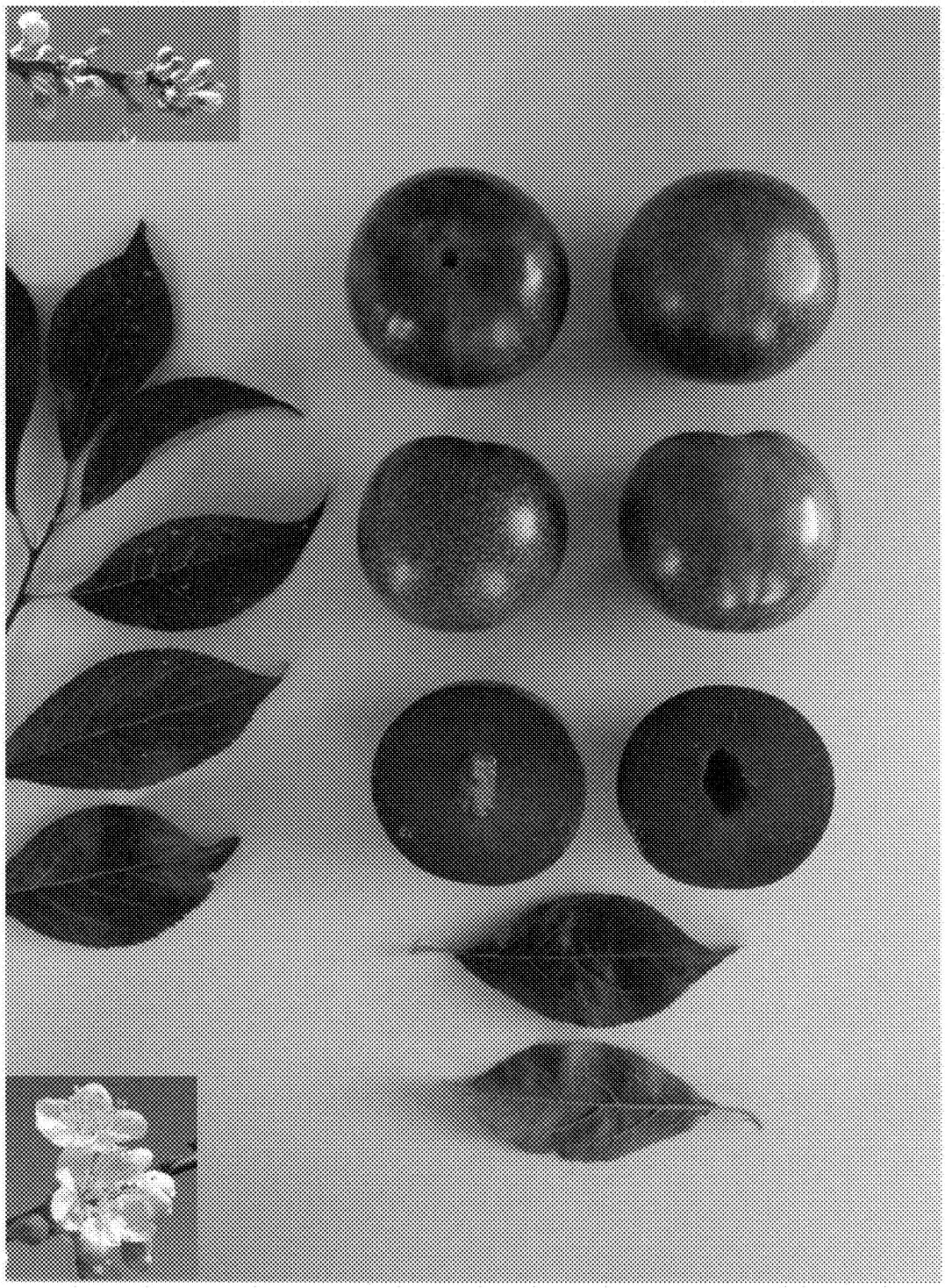

* * * * *